United States Patent
Wool

[11] Patent Number: 5,882,193
[45] Date of Patent: Mar. 16, 1999

[54] PLATED ORTHODONTIC APPLIANCE

[76] Inventor: Arthur L. Wool, 267 Faust Rd., Sinking Spring, Pa. 19608

[21] Appl. No.: 50,414

[22] Filed: Mar. 31, 1998

[51] Int. Cl.$^6$ .................................................. A61C 3/00
[52] U.S. Cl. ........................................................ 433/20
[58] Field of Search ........................................... 433/20

[56] References Cited

U.S. PATENT DOCUMENTS

| | | | |
|---|---|---|---|
| 5,092,941 | 3/1992 | Miura | 433/20 |
| 5,399,088 | 3/1995 | Mechley | 433/20 |

*Primary Examiner*—John J. Wilson
*Attorney, Agent, or Firm*—Antonelli, Terry, Stout & Kraus, LLP

[57] ABSTRACT

The present invention provides an orthodontic metal arch wire having a wire comprising a metal alloy, e.g., "shape memory" alloys, formed into an arch shape, and a metal layer provided on at least a portion of the wire such that an auxiliary part either is to or can be soldered to the metal layer. The metal layer provided on the arch wire can be a noble metal layer, e.g., gold, platinum, rhodium and palladium, or a layer of tin-nickel or palladium-nickel. An auxiliary part, such as a post, hook or loop, can then be soldered or brazed to the metal layer.

17 Claims, 1 Drawing Sheet

PLATED ORTHODONTIC APPLIANCE

BACKGROUND OF THE INVENTION

The present invention relates to an orthodontic appliance, more particularly orthodontic arch wires and orthodontic brackets, having a special coating or plating thereon.

As is well known in the art, orthodontic appliances, such as orthodontic metal arch wires and orthodontic brackets, can be made of stainless steel. More recently, however, improved arch wires have been made of so-called "shape memory" alloys. Before heat setting, the alloy can be bent and shaped, resulting in permanent conformation changes. If the alloy is reshaped after heat setting, it seeks to return to its original conformation. These properties are utilized in orthodontic arch wires in that, in the patient's mouth, the wire seeks to the return to its original conformation, thereby providing the necessary forces to patient's teeth.

Orthodontic arch wires made of such "shape memory" alloys are also known as superelastic or semi-superelastic arches. Examples of such arches include those made of a nickel-titanium alloy such as Nitinol sold by Unitek Corporation.

As noted in U.S. Pat. No. 5,399,087 and 5,538,422 to Arndt, it has not been possible to weld metal to arches made of "shape memory" alloys. Thus, it is not possible to weld or solder an auxiliary part, such as a post, hook or loop, to such arch wires. Rather, it has been necessary to use crimp tube adapters or, as disclosed in the Arndt patent, a sheath insert in order to secure auxiliary parts to "shape memory" arches.

Therefore, it is desirable to provide an orthodontic metal arch wire, including an arch wire made of a "shape memory" alloy, to which an auxiliary part can be or is soldered.

It is also desired to provide an orthodontic appliance, e.g., an orthodontic metal arch wire or bracket, whether made of stainless steel or a shape memory alloy, which has a bright, smooth and easy to clean surface, thereby improving aesthetics, reducing corrosion, and reducing the coefficient of friction of the wire surface.

SUMMARY OF THE INVENTION

Thus, the present invention provides an orthodontic metal arch wire having a wire comprising a metal alloy, e.g., "shape memory" alloys, formed into an arch shape, and a metal layer provided on at least a portion of the wire such that an auxiliary part either is to or can be soldered to the metal layer. The metal layer provided on the arch wire can be a noble metal layer, e.g., gold, platinum, rhodium and palladium, or a layer of tin-nickel or palladium-nickel. An auxiliary part, such as a post, hook or loop, can then be soldered to the metal layer.

DETAILED DESCRIPTION OF THE PREFERRED EMBODIMENTS

Figure 1:
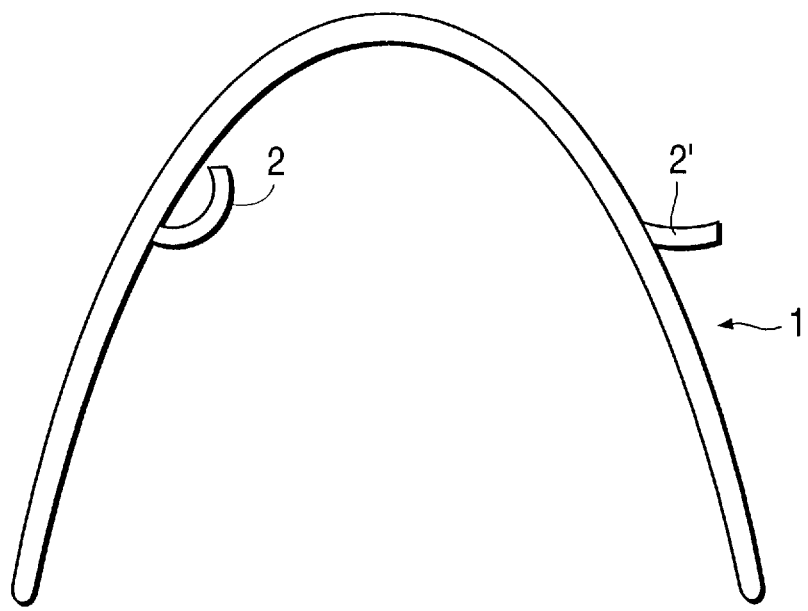
FIG. 1 is a perspective view of the arch wire of the present invention.
Figure 2:
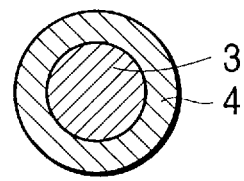
FIG. 2 is a cross-sectional view of the arch wire of the present invention.

The arch wire of the present invention, generally designated by the reference numeral 1, can be provided with auxiliary parts 2,2', such as posts, hooks, loops, etc., if desired, as shown in FIG. 1. As shown in FIG. 2, the arch wire 1 comprises a wire core 3 with a metal or metal alloy layer 4 provided thereon.

Applicant has found that arches made of shape memory alloys, such as nickel-titanium, have surfaces which, though ostensibly clean and free of any impurities, are actually covered by oxides. Such oxides are produced by the exposure to atmosphere and, especially, are produced during the heat setting of the arches. While it is common practice to clean off the dark stain of oxidization by short immersion in hydrofluoric acid, followed by washing, this process leaves the surface with a slightly etched effect rather than a preferred bright shine. Moreover, the process does not render the surface such that it can accept solder. Therefore, it is not possible to solder auxiliary parts, such a posts, hooks or loops to shape memory arches.

Applicant has found that providing certain metal layers on the surface of shape memory arches allows auxiliary parts to be soldered to the metal layer. The present invention contemplates the use of coatings of noble metal, e.g., gold, platinum, rhodium and palladium, tin-nickel and palladium-nickel as a coating on all or a portion of the arch wire in order to provide a surface onto which an auxiliary part can be soldered.

Before coating the arch wire with the noble metal, tin-nickel or palladium-nickel, the surface of the arch wire must be adequately prepared. Oxides on the surface can be removed by reducing agents, such as solutions of strong acid salts or the acids themselves. Certain passive or non-platable surfaces such as stainless steel are rendered oxide free (activated) by hydrochloric acid. Shape memory alloys, such as nickel-titanium alloys, must have their surfaces activated by reducing agents, e.g., ammonium bifluoride. Hydrochloric acid used as an activating agent is normally employed at a pH of about 1.3. Ammonium bifluoride can be used as a solution of 4 to 6 ounces/gallon of water.

After surface activation, the arch wires can be metal plated by the usual methods employed for electroplating. The entire arch wire can be plated by the usual plating techniques or specific areas of the arch wire can be coated by a localized brush or small area plating device.

Suitable metals for plating on the arch wire include noble metals, e.g., gold, platinum, rhodium and palladium, and tin-nickel and palladium-nickel. A suitable tin-nickel plating bath is "Techni Tin-Nickel" sold by Technic Inc. of Cranston, R.I. Such a plating bath will yield a uniform, bright, tin-nickel deposit containing approximately 65% by weight tin and 35% by weight nickel. A suitable plating bath to deposit palladium nickel is "Technic Palladium-Nickel VHS" sold by Technic, Inc. of Cranston, R.I.; this electroplating solution deposits a palladium-nickel alloy whose composition can be varied from 70% to 90% palladium by varying the solution pH. For example, at pH 7 or lower, the palladium-nickel ratio is on the order of 75–25 or lower; at pH 8.5 or above, the ratio is approximately 90/10. For an 80/20 deposit, the pH should be maintained at about 7.5–8.0. The pH may be raised if necessary with ammonium hydroxide or lowered with dilute hydrochloric acid.

When applied to orthodontic appliances, e.g., arch wires and brackets, the tin-nickel or palladium-nickel plate provides a smooth, bright, clean surface which reduces the coefficient of friction of the surface as well as enhances the cleaning ability. The tin-nickel or palladium-nickel plate does not change the wire or bracket color as does gold. This is especially useful to improve the appearance of cast brackets which are notoriously dull and uneven and the appearance of titanium brackets are difficult to polish to a shiny, bright surface. The plated surface also provides a solderable surface to which auxiliary parts such as posts, hooks, loops, etc. can be soldered or brazed. Soldering of such auxiliary parts can be conducted by usual soldering or brazing techniques using known soldering or brazing compositions or pastes. For example, applicant has effectively soldered auxiliary parts to the metal plated arch wires described above using a brazing paste comprising 35 wt. % flux (serving as an antioxidant, surface cleansing agent and carrying agent) and 65 wt % metal (the 65 wt. % metal being itself comprised of 50 wt. % silver, 28 wt. % zinc, 20 wt. % copper and 2 wt. % nickel) sold by Fusion Inc.

While the present invention has been described in detail and pictorially in the accompanying drawings it is not limited to such details since many changes and modifications recognizable to those of ordinary skill in the art may be made to the invention without departing form the spirit and the scope thereof.

I claim:

1. An orthodontic metal arch wire, comprising:
   a wire comprising a metal alloy formed into an arch shape;
   a layer of a noble metal provided on at least a portion of the wire; and
   an auxiliary part soldered to the layer of noble metal.

2. An orthodontic metal arch wire according to claim 1, wherein the metal alloy is a superelastic or semi-superelastic shape memory alloy.

3. An orthodontic metal arch wire according to claim 2, wherein the metal alloy comprises nickel and titanium.

4. An orthodontic metal arch wire according to claim 3, wherein the noble metal is selected from the group consisting of gold, platinum, rhodium and palladium.

5. An orthodontic metal arch wire according to claim 4, wherein the noble metal is gold.

6. An orthodontic metal arch wire according to claim 1, wherein the auxiliary part is selected from the group consisting of a post, a hook and a loop.

7. An orthodontic metal arch wire according to claim 1, wherein the layer of noble metal is plated on the entire surface of the wire.

8. An orthodontic metal arch wire according to claim 1, wherein the metal alloy is stainless steel.

9. An orthodontic metal arch wire according to claim 8, wherein the noble metal is selected from the group consisting of gold, platinum, rhodium and palladium.

10. An orthodontic metal arch wire according to claim 9, wherein the noble metal is gold.

11. An orthodontic metal arch wire, comprising:
    a wire comprising a metal alloy formed into an arch shape; and
    a layer of a tin-nickel or palladium-nickel provided on at least a portion of the wire.

12. An orthodontic metal arch wire according to claim 11, further comprising an auxiliary part soldered to the layer of tin-nickel or palladium-nickel.

13. An orthodontic metal arch wire according to claim 12, wherein the auxiliary part is selected from the group consisting of a post, a hook and a loop.

14. An orthodontic metal arch wire according to claim 11, wherein the metal alloy is a superelastic or semi-superelastic shape memory alloy.

15. An orthodontic metal arch wire according to claim 11, wherein the metal alloy comprises nickel and titanium.

16. An orthodontic metal arch wire according to claim 11, wherein the layer of tin-nickel or palladium-nickel is plated on the entire surface of the wire.

17. An orthodontic metal arch wire according to claim 11, wherein the metal alloy is stainless steel.

* * * * *